United States Patent
Lindacher et al.

(10) Patent No.: US 7,562,982 B2
(45) Date of Patent: Jul. 21, 2009

(54) GENERALIZED PRESBYOPIC CORRECTION METHODOLOGY

(75) Inventors: Joseph M. Lindacher, Suwanee, GA (US); Rafael V. Andino, Lawrenceville, GA (US); Scott R. Robirds, Alpharetta, GA (US); Teresa DeCenzo-Verbeten, Norcross, GA (US)

(73) Assignee: Novartis AG, Basel (CH)

( * ) Notice: Subject to any disclaimer, the term of this patent is extended or adjusted under 35 U.S.C. 154(b) by 42 days.

(21) Appl. No.: 12/004,243

(22) Filed: Dec. 20, 2007

(65) Prior Publication Data

US 2008/0165324 A1 Jul. 10, 2008

Related U.S. Application Data

(60) Provisional application No. 60/882,950, filed on Dec. 31, 2006.

(51) Int. Cl.
*A61B 3/00* (2006.01)
*G02C 7/02* (2006.01)

(52) U.S. Cl. ................ 351/246; 351/159

(58) Field of Classification Search ............. 351/246, 351/247, 159, 168–172; 359/642, 900
See application file for complete search history.

(56) References Cited

U.S. PATENT DOCUMENTS

| | | | | |
|---|---|---|---|---|
| 4,861,156 | A | 8/1989 | Terry | 351/243 |
| 5,777,719 | A | 7/1998 | Williams et al. | 351/212 |
| 6,095,651 | A | 8/2000 | Williams et al. | 351/246 |
| 6,338,559 | B1 | 1/2002 | Williams et al. | 351/212 |
| 6,428,533 | B1 | 8/2002 | Bille | 606/11 |
| 6,572,230 | B2 | 6/2003 | Levine | 351/221 |
| 6,582,079 | B2 | 6/2003 | Levine | 351/221 |
| 6,595,643 | B2 | 7/2003 | Levine | 351/221 |
| 6,609,794 | B2 | 8/2003 | Levine | 351/221 |
| 7,111,938 | B2 | 9/2006 | Andino et al. | 351/212 |
| 7,195,354 | B2 | 3/2007 | Olivier et al. | 351/205 |
| 2003/0223037 | A1 | 12/2003 | Chernyak | 351/209 |
| 2004/0008323 | A1 | 1/2004 | Williams | 351/212 |
| 2004/0100619 | A1 | 5/2004 | Olivier et al. | 351/221 |
| 2005/0030474 | A1 | 2/2005 | Sumiya | 351/211 |
| 2006/0023163 | A1 | 2/2006 | Foster | 351/246 |
| 2006/0232846 | A1 | 10/2006 | Himmer et al. | 359/224 |

(Continued)

OTHER PUBLICATIONS

Imagine Eyes, Mirao 52-d Deformable Membrane Mirror, 2005, 1 page.

(Continued)

*Primary Examiner*—William C Choi
*Assistant Examiner*—Jack Dinh
(74) *Attorney, Agent, or Firm*—Robert Ambrose (57) ABSTRACT

An adaptive optics phoropter is aligned with a Badal optometer and an adjustable aperture component to subjectively determine an optimal vision correction as a power profile for an ophthalmic lens or ablating a cornea. The optimal power profile is preferably determined in an iterative process by adjusting the vergence of the Badal optometer and aperture size of the adjustable aperture component for power profiles with presbyopic power zones having different amplitudes, shapes, widths, and/or de-centering. Also included is a method of recursively computing a refractive surface with a regular presbyopic power zone (e.g., according to the optimal power profile) and adding it onto an underlying irregular Zernike-basis-set aberration-corrected surface in a linear fashion for fabricating an ophthalmic lens.

10 Claims, 6 Drawing Sheets

U.S. PATENT DOCUMENTS

2006/0238710 A1    10/2006    Dick et al. .................. 351/211

OTHER PUBLICATIONS

Imagine Eyes, Mirao 52-d Deformable Membrane Mirror, Adaptive Optics Adapted to Eyecare, 2006, 1 page.

Olivier et al., "Eyes Can See Clearly Now," Science & Technology Review, 2003, pp. 12 and 13.

Prieto et al., "Adaptive Optics with a Programmable Phase Modulator: Applications in the Human Eye," Optics Express, 2004, vol. 12, pp. 4059-4071.

R & D Magazine, "Vision Correction in the 21st Century," 2006, 1 page.

GENERALIZED PRESBYOPIC CORRECTION METHODOLOGY

CROSS-REFERENCE TO RELATED APPLICATION

This application claims the benefits under 35 USC 119(e) of the U.S. Provisional Patent Application No. 60/882,950 filed Dec. 31, 2006 herein incorporated by reference in its entirety.

TECHNICAL FIELD

The present invention relates generally to the field of ophthalmic lenses and, more particularly, to using adaptive optics to subjectively adapt a subject's vision almost simultaneously to produce optimally corrected vision with an optimal power profile, and recursively determining a correction surface based on the optimal power profile for fabricating a lens.

BACKGROUND OF THE INVENTION

Contact lenses are widely used for correcting many different types of vision deficiencies. These include defects such as near-sightedness and far-sightedness (myopia and hypermetropia, respectively), astigmatism vision errors, and defects in near range vision usually associated with aging (presbyopia). Current opinion holds that presbyopia occurs as a person ages when the lens of eye begins to crystallize and lose its elasticity, eventually resulting in the eye losing the ability to focus on nearby objects.

Some presbyopic persons have both near-vision and far-vision defects, requiring bifocal lenses to properly correct their vision. Many people prefer wearing contact lenses to correct their vision rather than bifocal eyeglasses. However, creating a bifocal or simultaneous vision lens for presbyopes entails finding "compromise" vision, i.e., vision that is acceptable in both near and far vision, but perfect in neither.

Testing refractive errors of the eye involves several tests, some of which are subjective, and others that are objective in nature. Objective refraction tests include the use of retinoscopy, phoropter systems, wavefront sensors, and autorefractors. A phoropter can be manipulated by a control unit so that an operator's movement can be minimized during the testing procedure (see U.S. Pat. No. 4,861,156, which is expressly incorporated by reference as if fully set forth herein).

Refractive errors in the eye may also be detected by using wavefront sensors, such as for example a Shack-Hartmann wavefront sensor. Measurements of the wavefront aberrations of the eye, to a high degree of precision, using an improved Hartmann-Shack wavefront sensor are described in U.S. Pat. No. 5,777,719, which is expressly incorporated by reference as if fully set forth herein. The wavefront sensor illuminates the retina with a narrow cone of light from an LED or laser. The refractive errors of the eyes are measured and computed as a power map or wavefront representation such as a basis set of the Zernike polynomials. Starting at the retina, an ideal wavefront is generated which passes through the optical path of the eye. As the wavefront exits the eye, it contains a complete map of the eye's aberrations for analysis by the sensor. Once the wavefront is received by the sensor, a complex series of analyses are performed to provide a "complete" picture of the eye's optical path.

Objective refraction tests often to not correlate with subjective sphero-cylindrical correction or presbyopic correction. Because vision is subjective, differences in an eye's aberration, the individual's neural processing, and the individual's visual requirements may limit the effectiveness of objective tests. Subjective eye tests are more interactive than objective tests and may provide better compensation for an eye's aberration, the individual's neural processing, and the individual's visual requirements. Subjective tests can be performed by using adaptive optic phoropters, for example. These are new devices that recently became commercially available.

In addition, even if the technology were currently available to accurately determine an ideal vision correction on a customized basis, the technology is not currently available to fabricate, in a practical way, an ophthalmic lens having a refractive surface with the correction that is stable and registered to an eye's line of sight.

Thus it can be seen that needs exist for improvements to ophthalmic methods and systems to optimally correct for aberrations in the eye and to fabricate complex lenses with the needed corrections to provide optimal vision. It is to such improvements that the present invention is primarily directed.

SUMMARY OF THE INVENTION

Generally described, in one aspect the present invention provides a system and method for determining an optimal power profile for an eye. The system and method are used to subjectively assess a person's vision in order to determine an optimal vision correction expressed as the optimal power profile. An ophthalmic lens can then be fabricated with the optimal power profile to provide improved visual acuity.

In one example embodiment, the system includes an adjustable vergence component, an adaptive optics phoropter, and a control system. The adjustable vergence component includes a displayable focusing target, and is preferably provided by a Badal optometer with vergence settings to simulate distance, intermediate, and near vision. The adaptive optics phoropter includes an ophthalmic wavefront sensor and an adaptive optics wavefront corrector. The adaptive optics phoropter measures aberrations in the eye, and the adaptive optics wavefront corrector generates a plurality of objective power profiles that blur the focusing target equivalently to an ophthalmic lens with corrections for the aberrations and with a presbyopic power zone. The adaptive optics wavefront corrector preferably includes at least one MEMS deformable mirror device or equivalent technology for wavefront manipulation. The power profiles generated by the adaptive optics wavefront corrector each have a different amplitude, shape, width, and/or de-centered shift for the presbyopic power zone. The control system includes a processor and programming that are operable to adjust the vergence of the focusing target between a plurality of vergence settings and to adjust the adaptive optics wavefront corrector for each of the power profiles. In this way, the subjective visual performance of the person's eyes can be assessed for each of the power profiles at each of the vergence settings in an iterative fashion until the optimal one of the power profiles is determined.

In addition, the system preferably includes an adjustable aperture component with an aperture. The control system is operable to adjust the size of the aperture between a plurality of aperture size settings. In this way, the subjective visual performance of the eye can be assessed for each of the power profiles at each of the aperture size settings in the iterative fashion until the optimal one of the power profiles is determined. For example, the aperture size settings may be selected to simulate daylight (photopic), intermediate (mesopic), and nighttime vision (scotopic).

In another aspect of the present invention, there is provided a method for determining an optimal power profile for an eye, and an ophthalmic lens including the optimal power profile determined by the method. The method includes the steps of (a) measuring aberrations of the eye; (b) generating a first power profile that blurs a focusing target equivalently to an ophthalmic lens with corrections for the aberrations and with a presbyopic power zone; and (c) accessing subjective visual performance of the eye for the power profile. The method further includes the steps of (d) generating a subsequent power profile that blurs the focusing target equivalently to the ophthalmic lens with corrections for the aberrations and with a presbyopic power zone; and (e) repeating steps (c) and (d) in an iterative fashion until the optimal one of the power profiles is determined.

Preferably, step (a) includes measuring aberrations by using an ophthalmic wavefront sensor. Also, steps (b) and (d) preferably include generating power profiles by using an adaptive optics wavefront corrector. In steps (b) and (d), the power profiles are each generated having a different amplitude, shape, width, and/or de-centered shift for the presbyopic power zone.

In step (c), accessing the person's subjective visual performance preferably includes accessing the person's subjective visual performance when the focusing target is viewed at a first vergence setting, adjusting the vergence to a second setting, and accessing the subjective visual performance at the second vergence setting. More preferably, step (c) further includes adjusting the vergence to a third setting and accessing subjective visual performance at the third vergence setting, with the three vergence settings selected to simulate distance, intermediate, and near vision. In addition, step (c) preferably includes accessing the person's subjective visual performance when the focusing target is viewed through an aperture at a first aperture size setting, adjusting the aperture size to a second setting, and accessing subjective visual performance at the second aperture size setting. More preferably, step (c) further includes adjusting the aperture size to a third setting and accessing subjective visual performance at the third aperture size setting, with the aperture size settings selected to simulate daylight, intermediate, and nighttime vision.

In yet another aspect of the present invention, there is provided a method of defining a complex refractive surface, an ophthalmic lens fabricated with the complex refractive surface, and a software product for describing a complex refractive surface that can be used to fabricate the lens. Preferably, the lens is fabricated of lathable silicon hydrogel by using a single-point diamond cutting system.

The method includes the steps of (a) determining a non-axi-symmetrical base refractive surface with correction for aberrations; (b) defining a plurality of radial and azimuthal meridians on the base surface; (c) along each meridian, superimposing an axi-symmetrical presbyopic power zone (e.g., according to the optimal power profile) onto the non-axi-symmetrical base refractive surface to generate a resultant surface; and (d) fabricating the ophthalmic lens with the resultant surface.

Preferably, step (a) includes determining the non-axi-symmetrical base refractive surface by using an ophthalmic wavefront sensor. Also, step (c) preferably includes applying a recursive function so that the power zone is built up along each meridian in a linear fashion. For example, the step (c) may further include using a NURBS model for surface construction by boundary curves for recursively adding the power zone onto each meridian on the base surface.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Unless defined otherwise, all technical and scientific terms used herein have the same meaning as commonly understood by one of ordinary skill in the art to which this invention pertains. Generally, the nomenclature used herein and the manufacturing procedures are well known and commonly employed in the art. Conventional methods are used for these procedures, such as those provided in the art and various general references.

Figure 1:
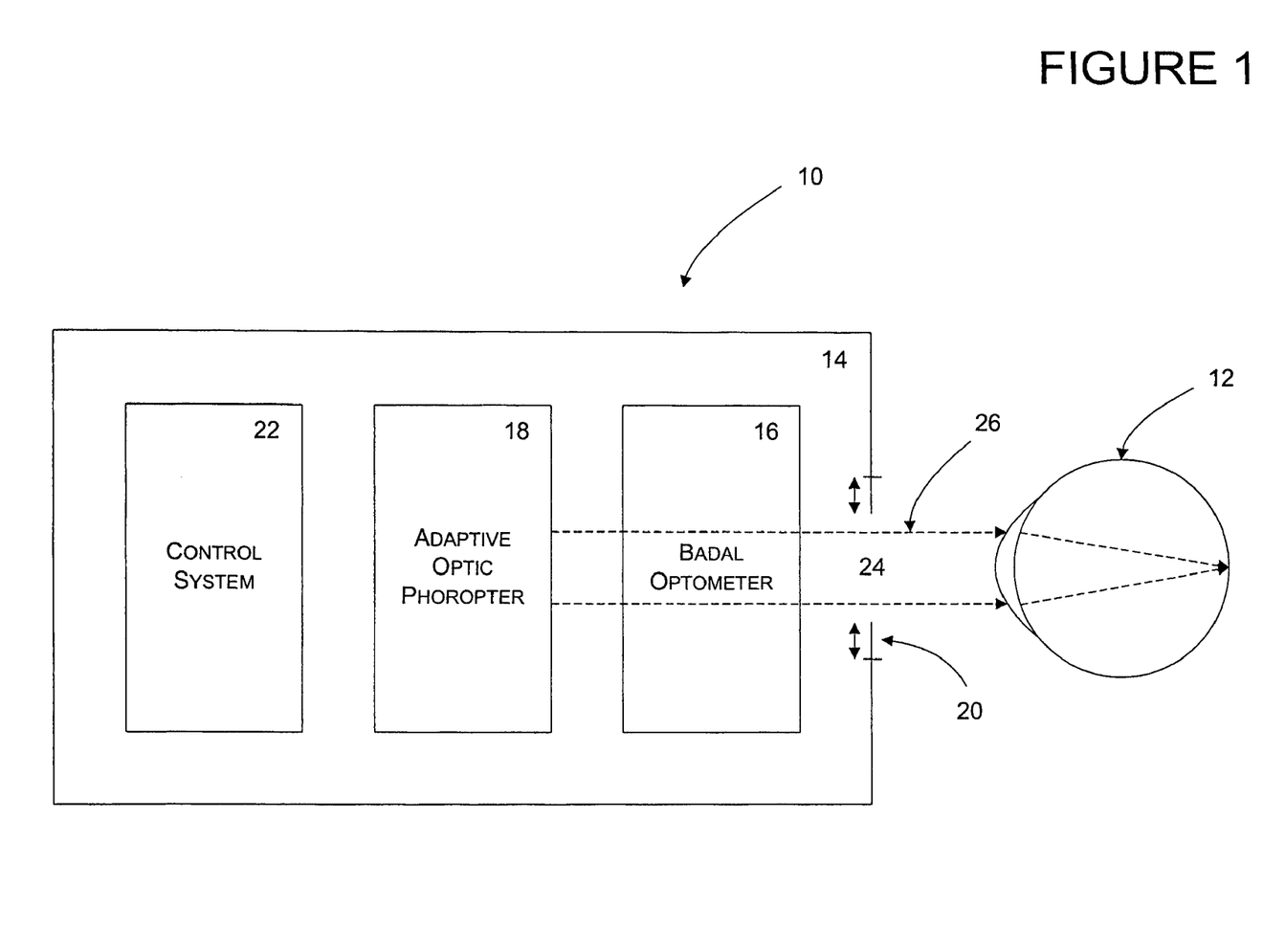
FIG. 1 is a block diagram schematically showing the major components of a system for determining an optimal power profile according to an example embodiment of the present invention.

FIG. 1 shows a system 10 for determining an optimal power profile for an eye 12 according to an example embodiment of the present invention. The system 10 is operable to subjectively assess a subject's vision in order to determine an optimal vision correction expressed as the optimal power profile. Thus, using the system 10, an operator can determine the optimal aberration profiles that produce through-focus vision with steady visual acuity. The system 10 can be used to determine the optimal "progressive" profiles and peripheral aberration structure for simultaneous vision presbyopic lenses. In addition, system 10 can be used to determine single vision corrections, because of the inclusion of the recently developed adaptive optic phoropter with high resolution and high-stroke MEMs devices, as described below.

The system 10 includes a housing 14 for an adjustable vergence component 16, an adaptive optics phoropter 18, an adjustable aperture component 20, and a control system 22. The housing 14 is preferably made of a durable material and construction to protect the other components, and may be of the same type as the housings of other conventional optometric devices in common use today.

The adjustable vergence component 16 includes a display for a focusing target (such as an image or an eye chart) for adjusting the vergence, whether physically repositioning the displayed target to different settings along the optic path or adjusting the size of the target so that it is perceived as having been repositioned to different settings. Preferably, the adjustable vergence component 16 is provided by a Badal optometer of the type well known in the art. Alternatively, another linear system that allows the vergence to be manipulated and the correct magnification maintained can be used.

The Badal optometer 16 preferably is modified for use in the present system 10 in that it's control software is combined with and/or interoperable with that of the control system 22. The optometer 16 is operable, in conjunction with the control system 22, to adjust the vergence for providing near and far field measurements. Preferably, the optometer 16 has settings for approximating at least three distances: distance vision, intermediate vision (for viewing a computer screen), and near vision (for reading). These types of vision may be approximated by resolving a user's vision at 0.0 diopters (D), 1.0 D, and 2.5 D, respectively. The term "resolve" means that the subject's current spherical correction is used to approximate the types of vision.

The adjustable aperture component 20 may be provided as a modular component and/or built into the housing 12. In either case, the adjustable aperture 20 is conjugate to the subject's pupil, positioned in the optical path 26 between the eye 12 and the Badal optometer 16, with the optometer being between the aperture and the adaptive optics phoropter 18. The adjustable aperture component 20 may be of a type used in conventional cameras (e.g., telephoto or wide-angle lenses), with an aperture 24 defined by a metal leaf diaphragm or an electro-optical means. The aperture 24 limits the amount of light and affects the depth of field. When the aperture 24 is adjusted smaller, the amount of light through it is decreased, the resolution is decreased, and the depth of field is increased, and when the aperture 24 is adjusted larger, the amount of light is increased, the resolution is increased, and the depth of field is decreased.

The size of the aperture 24 is adjusted by the control system 22 to various sizes for assessing vision in different light conditions. Preferably, the aperture 24 is adjustable to diameter settings of about 2.5 mm (for simulating bright daylight conditions), about 4.0 mm (for simulating medium-light conditions such as dawn, dusk, and poorly lit indoor areas), and about 6.0 mm (for simulating nighttime low-light conditions). In this way, the control system 22 adjusts the size of the aperture 24 to simulate different light conditions to optimally assess vision, instead of the operator having to constantly turn the lights in the room down and/or off and waiting for the subject's pupils to adjust before continuing with the vision assessment.

The adaptive optics phoropter 18 is selected for use in subjectively measuring the refractive error in the eye 12. Adaptive optics technology compensates for optical aberrations by controlling the phase of the light waves, or wavefronts incident on the retina—much like waves breaking on a shoreline. The optical structures in the eye, particularly the cornea and lens, can distort these wavefronts and thus produce the aberrations.

The adaptive optics phoropter 18 includes a wavefront sensor and an adaptive optics wavefront corrector. The wavefront sensor measures aberrations in the eye 12 and the wavefront corrector hardware compensates for the distortion. The adaptive optics phoropter 18 may be of a conventional type known in the art. For example, the adaptive optics phoropter 18 may be of the type developed by Lawrence Livermore National Laboratory (California).

The wavefront sensor may be of a conventional type known in the art. One suitable wavefront sensor that can be incorporated into the adaptive optics phoropter 18 is described in U.S. Pat. No. 5,777,719 to Williams, which is hereby incorporated by reference herein, and another is commercially available under the brand name ZYWAVE by Bausch & Lomb Incorporated (Rochester, N.Y.). The wavefront sensor generates infrared light that is directed at the subject's eye 12. This infrared light preferably has a wavelength of about 850 nm. The wavefront sensor then senses the aberrations of the eye.

The adaptive optics wavefront corrector is operable to create high spatial frequency refractive errors, and its control software preferably includes phase-wrap capability, so that it can create any or most any type of refractive error—including high spatial frequency refractive errors not found naturally in the human visual system. The adaptive optics wavefront corrector hardware may be of a conventional type known in the art, and may include deformable mirrors and/or MEMS devices. Deformable mirror MEMS devices have mirrors and actuators that push on or otherwise manipulate the mirrors to change their curvature. One known suitable deformable membrane mirror device is commercially available under the brand MIRAO from Imagine Eyes (Orsay, France). This is a high-stroke device, so the mirror can be deformable to a high degree of curvature, making it suitable for use in determining single vision corrections for high-magnitude aberrations farther out from the center of the pupil. Alternatively, the adaptive optics corrector hardware may be a commercially available a spatial light modulator or low-stroke deformable mirror device. Such low-stroke deformable mirrors are primarily suitable for determining low-magnitude aberrations for optimal presbyopic profiles near the center of the pupil.

The adaptive optics phoropter 18 preferably is modified for use in the present system 10 in that it's control software is combined with and/or interoperable with that of the control system 22. A person of ordinary skill in the art will understand how to make the needed modifications. The adaptive optics phoropter 18 is operable by the control system 22 to allow the wavefront sensor to iterate until the adaptive optics hardware changes such that it projects a substantially aberration-free image back to the user.

The control system 22 includes a computer processor and a storage device with software for controlling the operation of the system 10. The control system 22 is operable to adjust the diameter of the aperture 24 to the settings for bright, medium, and low light conditions. In addition, the control system 22 is operable to control the display of the focusing target and to adjust the Badal optometer 16 to provide the vergence for near, intermediate, and distance vision. Furthermore, the control system 22 is operable in a closed loop to cause the wavefront sensor to iterate until the adaptive optics hardware changes such that it projects a substantially aberration-free focusing target back to the user's eye 12. The control system 22 modifies the alignment of the power profiles relative the eye's line-of-sight to adjust the decentering of the presbyopic power zone. Also, the control system 22 preferably includes phase-wrap software to extend the dynamic range when using the adaptive optics phoropter 18, if the adaptive optics wavefront corrector is a spatial light modulator. It will be understood that the some of these features, for example the adjustment of the aperture and the vergence, can be omitted from the control system 22 and performed manually. Preferably, the spherical refractive error term (Zernike index 20), is adjusted out with the optometer 16 and the all other Zernike terms are manipulated with the adaptive optics wavefront corrector.

Figure 2:
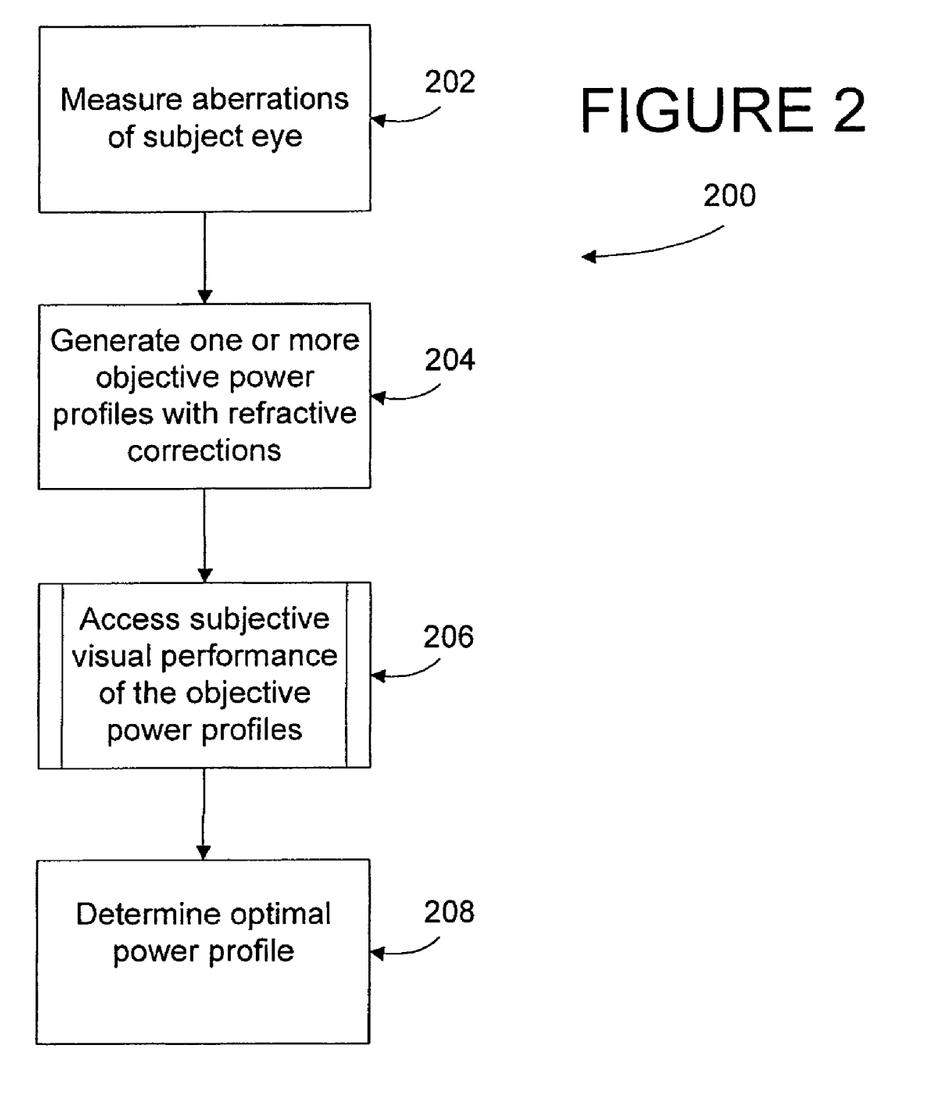
FIG. 2 is a flow diagram showing a method of determining an optimal power profile according to an example embodiment of the present invention.

Referring now to FIG. 2, there is shown a method 200 of determining an optimal power profile for an eye according to an example embodiment of the present invention. The method 200 can be carried out by use of the system 10 or by other similar systems including the components similar to those of the system 10. In addition, it will be understood that the control system 22 is configured and programmed to operate the other components of the system 10 to carry out the method 200.

The method 200 includes at step 202 measuring the natural aberrations of a subject's eye. For example, when using the system 10 described herein, this is done by the wavefront sensor of the adaptive optics phoropter 18 in conjunction with the control system 22. Next, at step 204, the wavefront corrector hardware of the adaptive optics phoropter 18, in conjunction with the control system 22, generates at least one and preferably a series of objective power profiles that blur the focusing target in an equivalent way that an ophthalmic lens would with corrections for the aberrations and with and an added power zone according to the power profiles. Each of the power profiles has a different amplitude, shape, width, and/or de-centered shift for the power zone. By knowing the subject's age or ADD requirement, the initial amplitude, diameter, and shape of the ADD power profile will be computed as a starting point. Based upon the subjective response the ADD power profile will be adjusted.

More specifically, the wavefront sensor identifies the positions and magnitudes of the aberrations, and the control system 22 determines a power profile with an appropriate adjustment to provide an aberration-corrected focusing target. I.e., the wavefront sensor determines how much the wavefront is distorted as it passes through the eye's cornea and lens. Then the computer of the control system 22 uses this information to create an internal, three-dimensional (3D) representation of the distorted wave. That 3D shape is then used to define the power profile and to instruct the adaptive optics hardware. In embodiments in which MEMs deformable mirror devices are used, the MEMS actuators are instructed to move to positions that will minimize the distortion and "flatten" the wavefront in the same way that a corrective ophthalmic lens would.

Aberrations of the eye are typically decomposed into sphero-cylindrical refractive errors. More recent technology, such as ophthalmic wavefront sensors of the type used in the adaptive optic phoropter, provides more resolution to determine a more exact refractive error pattern. An ophthalmic lens can be designed using a Zernike basis set to cancel the eye's aberrations, and, in turn, to optimize vision. Table 1 lists the Zernike functions up to the seventh order:

TABLE 1

Listing of Zernike Polynomials in Polar Coordinates up to $7^{th}$ order (36 terms)

| j = index | n = order | m = frequency | $Z_n^m (\rho, \theta)$ |
|---|---|---|---|
| 0 | 0 | 0 | 1 |
| 1 | 1 | −1 | $2 \rho \sin \theta$ |
| 2 | 1 | 1 | $2 \rho \cos \theta$ |
| 3 | 2 | −2 | $\sqrt{6} \rho^2 \sin 2\theta$ |
| 4 | 2 | 0 | $\sqrt{3} (2\rho^2 - 1)$ |
| 5 | 2 | 2 | $\sqrt{6} \rho^2 \cos 2\theta$ |
| 6 | 3 | −3 | $\sqrt{8} \rho^3 \sin 3\theta$ |
| 7 | 3 | −1 | $\sqrt{8} (3\rho^3 - 2\rho) \sin \theta$ |
| 8 | 3 | 1 | $\sqrt{8} (3\rho^3 - 2\rho) \cos \theta$ |
| 9 | 3 | 3 | $\sqrt{8} \rho^3 \cos 3\theta$ |
| 10 | 4 | −4 | $\sqrt{10} \rho^4 \sin 4\theta$ |
| 11 | 4 | −2 | $\sqrt{10} (4\rho^4 - 3\rho^2) \sin 2\theta$ |
| 12 | 4 | 0 | $\sqrt{5} (6\rho^4 - 6\rho^2 + 1)$ |
| 13 | 4 | 2 | $\sqrt{10} (4\rho^4 - 3\rho^2) \cos 2\theta$ |
| 14 | 4 | 4 | $\sqrt{10} \rho^4 \cos 4\theta$ |
| 15 | 5 | −5 | $\sqrt{12} \rho^5 \sin 5\theta$ |
| 16 | 5 | −3 | $\sqrt{12} (5\rho^5 - 4\rho^3) \sin 3\theta$ |
| 17 | 5 | −1 | $\sqrt{12} (10\rho^5 - 12\rho^3 + 3\rho) \sin \theta$ |
| 18 | 5 | 1 | $\sqrt{12} (10\rho^5 - 12\rho^3 + 3\rho) \cos \theta$ |
| 19 | 5 | 3 | $\sqrt{12} (5\rho^5 - 4\rho^3) \cos 3\theta$ |
| 20 | 5 | 5 | $\sqrt{12} \rho^5 \cos 5\theta$ |
| 21 | 6 | −6 | $\sqrt{14} \rho^6 \sin 6\theta$ |
| 22 | 6 | −4 | $\sqrt{14} (6\rho^6 - 5\rho^4) \sin 4\theta$ |
| 23 | 6 | −2 | $\sqrt{14} (15\rho^6 - 20\rho^4 + 6\rho^2) \sin 2\theta$ |
| 24 | 6 | 0 | $\sqrt{7} (20\rho^6 - 30\rho^4 + 12\rho^2 - 1)$ |
| 25 | 6 | 2 | $\sqrt{14} (15\rho^6 - 20\rho^4 + 6\rho^2) \cos 2\theta$ |
| 26 | 6 | 4 | $\sqrt{14} (6\rho^6 - 5\rho^4) \cos 4\theta$ |
| 27 | 6 | 6 | $\sqrt{14} \rho^6 \cos 6\theta$ |
| 28 | 7 | −7 | $4 \rho^7 \sin 7\theta$ |
| 29 | 7 | −5 | $4 (7\rho^7 - 6\rho^5) \sin 5\theta$ |
| 30 | 7 | −3 | $4 (21\rho^7 - 30\rho^5 + 10\rho^3) \sin 3\theta$ |
| 31 | 7 | −1 | $4 (35\rho^7 - 60\rho^5 + 30\rho^3 - 4\rho) \sin \theta$ |
| 32 | 7 | 1 | $4 (35\rho^7 - 60\rho^5 + 30\rho^3 - 4\rho) \cos \theta$ |
| 33 | 7 | 3 | $4 (21\rho^7 - 30\rho^5 + 10\rho^3) \cos 3\theta$ |
| 34 | 7 | 5 | $4 (7\rho^7 - 6\rho^5) \cos 5\theta$ |
| 35 | 7 | 7 | $4 \rho^7 \cos 7\theta$ |

Correcting for astigmatism has traditionally meant correcting the second-order astigmatic aberrations, which are Zernike mode indices 3 and 5. And correcting for myopia and hypermetropia has traditionally been done by correcting for defocus. Defocus is composed of axi-symmetrical Zernike indices 4, 12 and 24, but Zernike index 4 is the primary spherical power component and is thus the only mode corrected for. Traditional phoropters are not able to measure aberrations of a higher order than second-order astigmatism and defocus. But the new wavefront sensors allow for measuring higher-order aberrations with high resolution, such as third-order coma (indices 7 and 8), fourth-order astigmatism (indices 11 and 13), fourth-order spherical aberration (index 12), and sixth-order spherical aberration (index 24).

Continuing with the method 200, at step 206, the subjective visual performance of the subject's eye is accessed and recorded for various power profiles, vergences, and/or aperture sizes. The better the registration of the power profiles to the visual axis, the better the subjective visual performance tends to be. The optimal power profile is determined at step 208 as the power profile that provides the best registration to the visual axis and/or for which the subject provides subjective feedback indicating the most preferred visual performance. The optimal power profile can be determined on an individual (custom) basis, or alternatively it can be determined from data taken from a large number of subjects. Then the optimal power profile can be saved in electronic format and provided (delivered on a portable storage device, sent over a computer network, etc.) to a manufacturer for fabrication of an ophthalmic lens.

Figure 3:
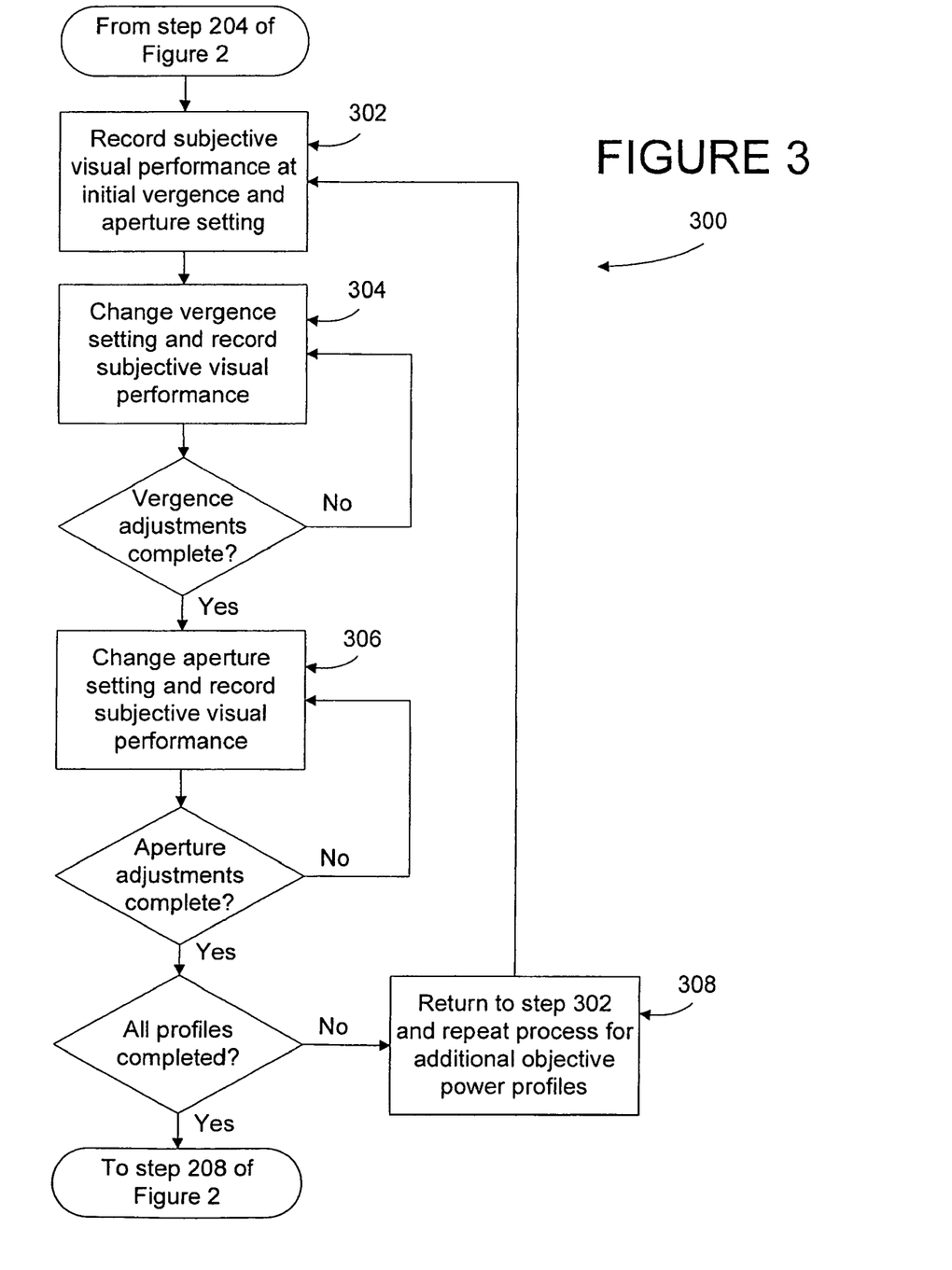
FIG. 3 is a flow diagram showing a closed-loop iterative method of accessing subjective visual performance according to the method of FIG. 2.

Preferably, the step 206 of accessing and recording the subjective visual is done in a closed-loop iterative process at various vergences and aperture sizes. As shown in FIG. 3, an example iterative method 300 is shown. At step 302, the subjective visual performance of the subject's eye is first accessed and recorded at one vergence and aperture setting. Then at step 304 the subjective visual performance of the subject's eye is accessed and recorded as the vergence setting of the Badal optometer or other adjustable vergence component is changed one or more times. For example, the vergence can be adjusted to settings for resolving a subject's vision at about 0.0 diopters (D), about 1.0 D, and about 2.5 D to approximate for distance, intermediate, and near vision, respectively. And at step 306 the subjective visual performance of the subject's eye is accessed and recorded as the aperture setting of the adjustable aperture component is changed one or more times. For example, the size of the aperture can be adjusted to settings of about 2.5 mm, about 4.0 mm, and about 6.0 mm, to approximate for typical bright daylight, medium-light, and nighttime low-light conditions, respectively. Preferably, the iterative process further includes at step 308 returning to step 302 to repeat these steps for additional power profiles at each vergence and aperture setting until the adaptive optics corrector hardware projects a substantially aberration-free focusing target (with the subjectively best compromise for presbyopic vision) back to the user. While this iterative process is performed automatically by the control system 22 in the described system 10, it will be understood that this process can be performed manually (by the physician/healthcare professional or by the subject directly) by making the needed adjustments to different vergence and aperture settings.

Figure 4:
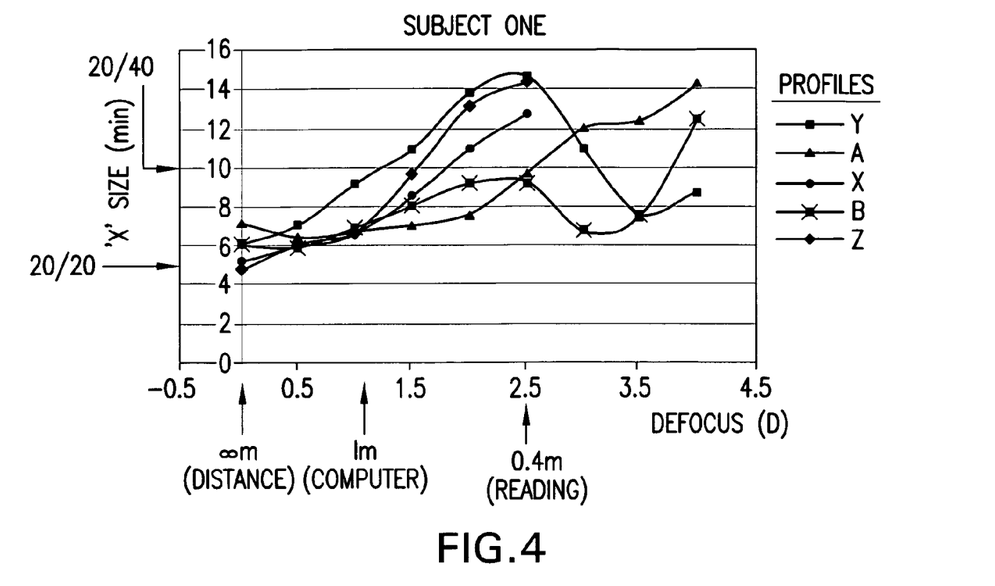
FIG. 4 is a graph of recorded measures of subjective visual acuity for a test subject using two power profiles according to an example system and method of the present invention.
Figure 5:
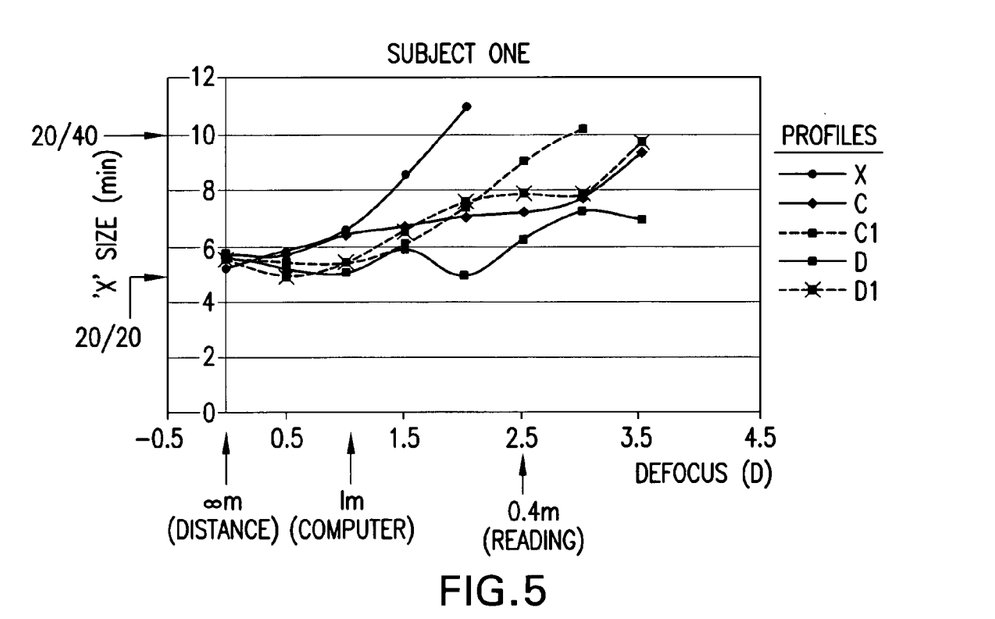
FIG. 5 is a graph of recorded measures of subjective visual acuity for the same test subject using four other power profiles according to an example system and method of the present invention.

FIGS. 4 and 5 illustrate test data for one test subject using the method 200 and a prototype of the system 10 in which the adaptive optics wavefront corrector hardware was a spatial light modulator with a phase-wrapping algorithm applied to extend the dynamic range of the system. These figures show a plot of the minimum angle of resolution (MAR), which is a measure of visual acuity, at different vergences for a set aperture (not at different aperture size settings). A MAR of 5 roughly corresponds to 20/20 vision, and a MAR of 10 roughly corresponds to 20/40 vision. The "x" axis is the vergence, with the unit being diopters, the reciprocal of the focal length measured in meters. And the "y" axis is the MAR, with the units being millimeters, as this is a measure of the height of the smallest character of the focusing target that the subject could correctly identify at 0.5 D incremental vergence steps. This test data represents the subjective feedback from the test subject for each of the tested power profiles.

Power profile X is the baseline control, as it includes a correction for spherical defocus only with no phase shift. Power profile Y is the same as that of a contact lens that is commercially available under the brand name "FOCUS DAILIES" from CIBA Vision Corporation (Duluth, Ga.). Power profile Z is that of a contact lens including correction for presbyopia only without correction for spherical defocus or any other Zernike modes.

Using the power profiles X, Y, and Z as references, several profiles were tested for comparison. Power profile A is a 1.5 D flattop (i.e., a step function) power profile with a 2.2 mm diameter width. Power profile B is a 3.0 D flattop power profile with a 2.2 mm diameter width. Power profile C is compound 2 D flattop power profile with a 2.2 mm diameter width. Power profile C1 is the same as power profile C, but de-centered 0.6 mm nasally. Power profile D is a 2.0 D flattop power profile with a 2.2 mm diameter width. Power profile D1 is the same as power profile D, but de-centered 0.6 mm nasally.

The data clearly show and allow for extrapolating that:

Peak ADD power profiles less than about 2.5 D, and preferably less that about 2.0 D, with the power profile being constant and tapering to the distance power, tend to provide for optimal visual performance by maintaining relatively constant visual acuity through the usable vergence. The larger the magnitude of the step function, the more compromise there is between near, intermediate, and distance vision for presbyopes. This is due to the tendency at higher diopters for the subject to experience a zone of poorer vision between two "sweet spots" of good vision. The best subjective results were obtained for profiles in which the MAR stayed close to 5 for up to about 2.0 to 2.5 D and then trailed upwardly smoothly.

Registration of the ADD or presbyopic zone(s) to the visual axis maximizes performance.

Power gradients from high peak ADD powers significantly degrade intermediate vision and have an effective near zone at too great a vergence (too close to the eye).

Varying photopic pupil diameters can be accounted for with varying diameter central zones.

Modified mono-vision enhanced with these derived simultaneous vision lenses will provide relatively constant visual acuity for older or absolute presbyopic subjects.

Figure 6A:
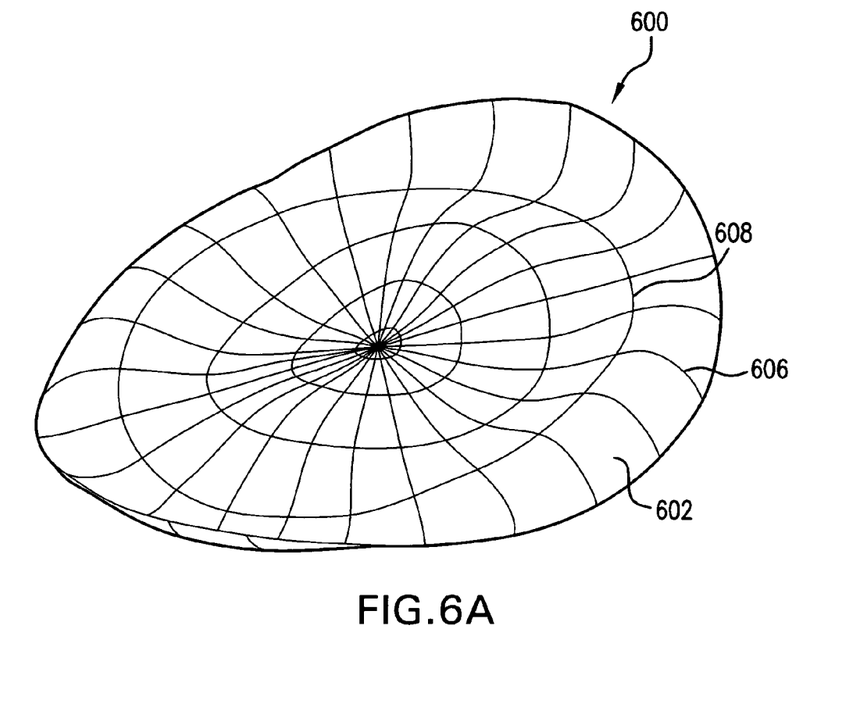
FIG. 6A is an ophthalmic lens having a regular presbyopic power zone added onto an irregular basis surface according to an example embodiment of the present invention.
Figure 6B:
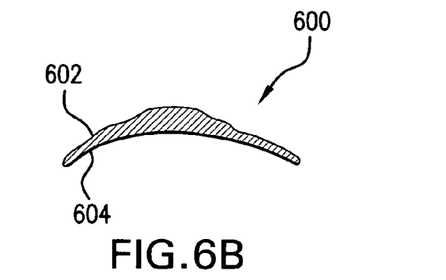
FIG. 6B is a cross-sectional view of the lens of FIG. 6A.
Figure 6C:
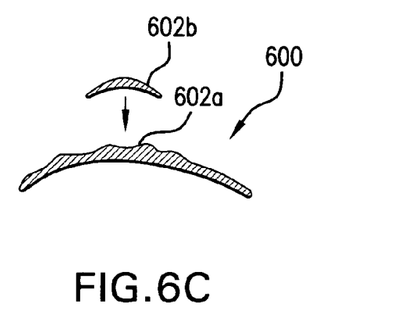
FIG. 6C is a cross-sectional view of the lens of FIG. 6A, showing the regular presbyopic power zone and the irregular basis surface onto which it is added.

Having described a system 10 and method 200 for determining an optimal power profile for an ophthalmic lens, a method for describing and fabricating the lens will now be described. FIGS. 6A-C show, as an example, one such lens 600. For a contact lens, the aberration correction is typically designed for and fabricated on the front refractive surface 602, whereas the posterior surface 604 can be conic or otherwise shaped to fit the subject eye's corneal topography. As shown with particularity in FIG. 6C, the depicted lens 600 has a progressive, axi-symmetrical power zone (such as for presbyopia) 602b, with a circular or elliptical boundary, added onto an irregular refractive surface 602a with corrections for Zernike aberrations.

As described above, Zernike polynomials are typically used to describe refractive errors for correcting with ophthalmic lenses. However, the Zernike basis set or surface function filters the high-spatial frequency features required for presbyopic vision correction. That is, the Zernike basis set for correcting for myopia or hypermetropia does not have terms, such as spline terms or terms with high-enough spatial resolution, to describe current or future "progressive" presbyopic lens design features, such as the depicted lens 600.

Figure 7:
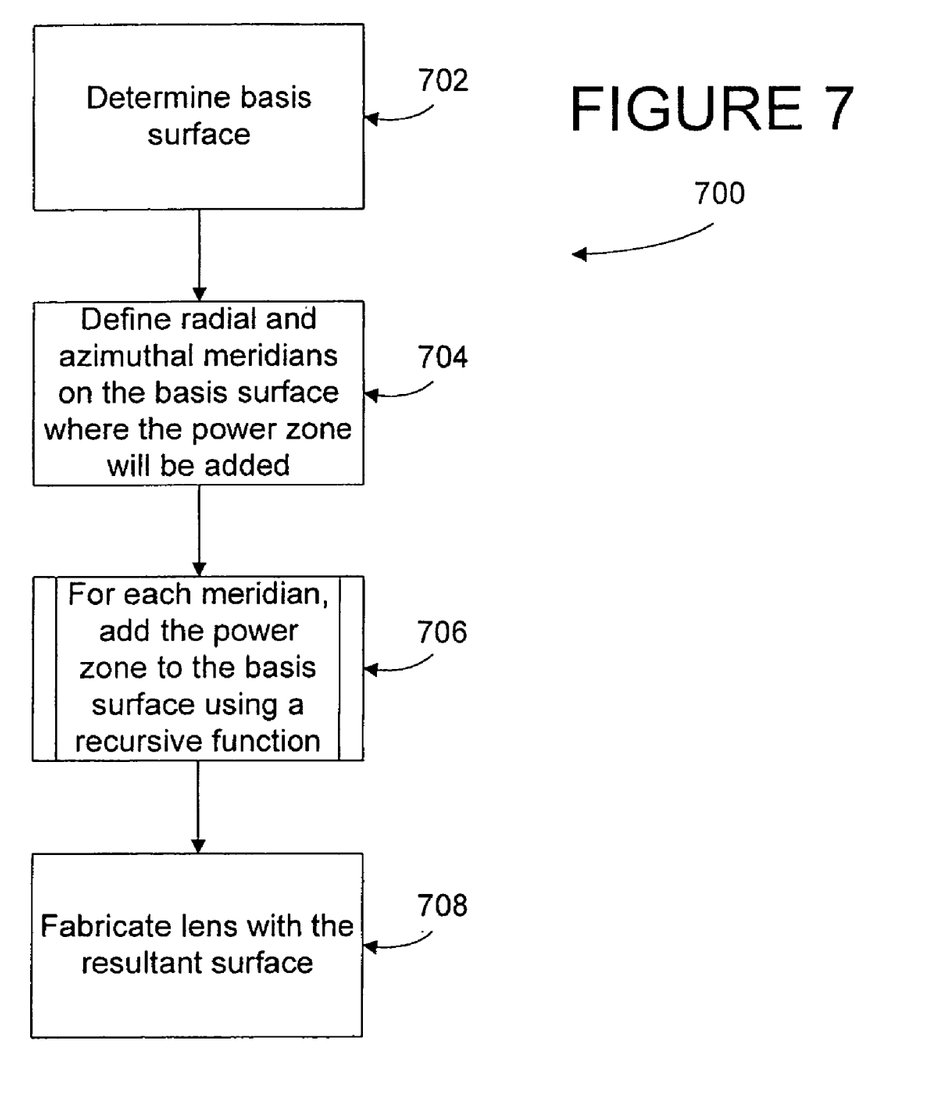
FIG. 7 is a flow diagram showing a method of adding a regular presbyopic power zone onto an irregular basis refractive surface according to an example embodiment of the present invention.

FIG. 7 shows an example method 700 for determining a resultant refractive surface profile for including in an ophthalmic lens or for use in ablating a cornea. The refractive surface can include the optimal power zone profile determined by the above-described system 10 and method 200. In particular, the refractive surface may comprise a progressive, regular, axi-symmetrical power zone 602b (according to the optimal power profile) added onto an irregular, non-axi-symmetrical, aberration-corrected, base refractive surface 602a. The method 700 can be used to construct single or multiple power zones on the basis surface. In addition, the added zone or zones can be central, concentric, non-concentric, and/or non-circular. Furthermore, the method can be used to describe toric lenses where the progressive profile must be fabricated on the same surface as the cylindrical or biconic surface. Moreover, the method can be used to describe custom presbyopic lenses, progressive lenses with zone offset on non-spherical surfaces, and toric and progressive features on the same surface.

The method 700 includes at step 702 determining a basis sphero-cylindrical or higher-order Zernike surface 602*a*, with correction for defocus (myopia or hypermetropia), astigmatism, coma, and/or other aberrations. This can be done using the ophthalmic wavefront sensor of the system 10 and method 200 described above. Then at step 704, a number of radial and azimuthal meridians 606 and 608 are defined on the basis surface 602*a* (see FIG. 6A). In a preferred embodiment (not shown), 16 radial meridians and 5 azimuthal meridians are defined within the area on the Zernike basis surface 602*a* where the power zone 602*b* is to be added.

At step 706, for each meridian, an axi-symmetrical power zone 602*b* is added to the basis surface 602*a*. This is done using a recursive function so that the power zone 602*b* is built up along each meridian in sequence in a linear fashion. The resultant front surface of the lens 600 where the power zone 602*b* is added is computed via a linear superposition of functions (curves or splines) such that the apex position of each radial meridian is equivalent and such that the resulting curvature produces the added power in addition to the basis surface corrections. The resultant front surface 602 of the lens 600 is smooth and tangent at each point. The amplitude, shape, diameter, and centering of the power zone 602*b* may be determined using the ophthalmic wavefront sensor and adaptive optics corrector of the system 10 and method 200 described above.

Steps 704 and 706 may be performed by software included in the control system 22 of the system 10 described above, or such software may be provided as a stand-alone software product for running on another computer such as one at a manufacturer of ophthalmic lenses. The software for recursively computing the resultant front surface 602 of the lens 600 preferably includes a non-uniform rational basis spline (NURBS) model for surface construction by boundary curves. NURBS is a well-known mathematical model commonly used in CAD systems for generating and representing free-form curves and modeling complex shapes based on spline curves, and a person of ordinary skill in the art would know how to adapt a commercially available NURBS program to carry out the method. A commercially available program that can be adapted for use in the method is sold under then brand name "POWER NURBS 2.0" and is provided by nPower Software, a division of Integrity Ware, Inc. (San Diego, Calif.). In addition, the major commercial CAD systems, such as those provided under the brand names "SOLID-WORKS" by SolidWorks Corporation (Concord, Mass.) and "PRO/ENGINEER" by Parametric Technology Corporation (PTC) (Needham, Mass.), operate on a NURBS kernel, and these systems are suitable for use in implementing the method.

The software can be stored on a computer-readable medium for use with a computing system (the control system 22 or a separate system, not shown). The computing system can comprise a general-purpose personal computer such as a desktop, laptop or handheld computer. Such a computing system includes a programmed processor system, a display, a keyboard, a mouse or similar pointing device, a network interface, a fixed-medium data storage device such as a magnetic disk drive, and a removable-medium data storage device such as a CD-ROM or DVD drive. Other elements commonly included in personal computers can also be included but are not detailed for purposes of clarity. Although not described individually for purposes of clarity, the programmed processor system includes a conventional arrangement of one or more processors, memories and other logic that together define the overall computational and data manipulation power of the computing system.

Although the described example embodiment includes a personal computer or similar general-purpose computer, in other embodiments it can comprise any other suitable system. In some embodiments, portions of such a computing system can be distributed among a number of networked computers, data storage devices, network devices, and other computing system elements. It should be noted that the software can be stored in a distributed manner and retrieved via the network interface from multiple sources on an as-needed basis. Similarly, it can be stored on multiple disks or other data storage media and retrieved or otherwise loaded into the computing system on an as-needed basis.

The user can interact with the computing system through a user interface in a conventional manner. The user interface can comprise, for example, a graphical user interface (GUI) that operates in accordance with standard windowing and graphical user interface protocols supported by MICROSOFT WINDOWS or a similar operating system. That is, the user can manipulate (e.g., open, close, resize, minimize, etc.) windows on the display, launch application software that executes within one or more windows, and interact with pictures, icons, and graphical control structures (e.g., buttons, checkboxes, pull-down menus, etc.) on the display using the mouse, the keyboard, or other input devices. The user interface can include not only the logic through which screen displays are generated and made viewable but also computational logic that generates and organizes, tabulates, etc., numerical values to be displayed or otherwise output. Similarly, the user interface can include logic for importing, exporting, opening, and closing data files.

The process by which the recursive function builds up the resultant surface is as flows. For each of the meridians on the underlying surface where the power zone is to be added, the height of the meridian is increased at each point on that meridian by the magnitude of the power zone profile at that point. The increased meridian height is calculated based upon the increased curvature along that meridian.

After the resultant front surface 602 has been described, at step 708 an ophthalmic lens is fabricated with the surface. An electronic data file including a description of the resultant surface can be delivered to the fabricator via the network connection, on a storage device, or otherwise. The lens is preferably fabricated of lathable silicon hydrogel. The lens fabrication can be done using conventional systems known in the art. Preferably, the lens is fabricated using an ultra-precision single-point diamond turning system, such as is described in U.S. Pat. No. 7,111,938 owned by Novartis AG, which is hereby incorporated by reference herein. For surface fabrication using such a device, compensation for anticipated fabrication errors is designed into the offset "progressive" meridians 606 of the lens 600. In particular, the meridians 606 are arranged so that their end points remain tangent. The elevation (curvature) of the offset meridians 606 is adjusted to compensate for the fabrication errors resulting from positive or negative movement of the oscillating tool. This is advantageous because fractions of a micron will affect the resulting optical power in a progressive type zone. The resultant optical power is proportional to the Laplacian of the surface function.

A resultant front surface described by the method 700, which may include an optimal power profile determined by the system 10 and/or method 200, can be practically implemented in several ways to provide optimal presbyopic correction and custom vision correction. An ophthalmic lens can be fabricated with a refractive surface conforming to the optimal power profile. Such ophthalmic lenses include single-vision (myopia or hypermetropia) contact lenses, simultaneous-vision (presbyopic) contact lenses, toric (astigmatism) contact lenses, phakic contact lenses, aphakic intraocular lenses (IOLs), and other contact lenses and IOLs. Alternatively, a cornea of can be ablated with a laser to conform to the resultant front surface, which may be based on the optimal power profile, in laser refractive surgery.

While the invention has been described with reference to preferred and example embodiments, it will be understood by those skilled in the art that a variety of modifications, additions and deletions are within the scope of the invention, as defined by the following claims.

What is claimed is:

1. A method of determining a resultant refractive surface, comprising:
    (a) determining a non-axi-symmetrical base refractive surface with correction for aberrations;
    (b) defining a plurality of radial and azimuthal meridians on the base surface; and
    (c) along each meridian, superimposing an axi-symmetrical power zone onto the non-axi-symmetrical base refractive surface to generate a resultant surface.

2. The method of claim 1, wherein step (a) includes determining the non-axi-symmetrical base refractive surface by using an ophthalmic wavefront sensor.

3. The method of claim 1, wherein step (b) includes defining 16 radial meridians and 5 azimuthal meridians on the base surface where the power zone is to be added.

4. The method of claim 1, wherein step (c) includes applying a recursive function to build up the power zone along each meridian in a linear fashion.

5. The method of claim 4, wherein step (c) further includes using a NURBS model for surface construction by boundary curves for recursively adding the power zone onto each meridian on the base surface.

6. A computer-readable medium encoded with computer-executable instructions for carrying out the method of claim 1.

7. The method of claim 1, further comprising (d) fabricating an ophthalmic lens with the resultant surface.

8. The method of claim 7, wherein step (d) includes fabricating the ophthalmic lens of lathable silicon hydrogel.

9. The method of claim 7, wherein step (d) includes fabricating the ophthalmic lens using a single-point diamond cutting system.

10. An ophthalmic lens fabricated by using the method of claim 7.

* * * * *